US007816407B2

(12) United States Patent
Crooks et al.

(10) Patent No.: US 7,816,407 B2
(45) Date of Patent: Oct. 19, 2010

(54) AGMATINE AND AGMATINE ANALOGS IN THE TREATMENT OF EPILEPSY, SEIZURE, AND ELECTROCONVULSIVE DISORDERS

(75) Inventors: Peter A. Crooks, Lexington, KY (US); Aimee K. Bence, Lexington, KY (US); David R. Worthen, Lexington, KY (US)

(73) Assignee: University of Kentucky Research Foundation, Lexington, KY (US)

( * ) Notice: Subject to any disclaimer, the term of this patent is extended or adjusted under 35 U.S.C. 154(b) by 1240 days.

(21) Appl. No.: 09/881,215

(22) Filed: Jun. 15, 2001

(65) Prior Publication Data

US 2002/0065323 A1    May 30, 2002

Related U.S. Application Data

(60) Provisional application No. 60/211,532, filed on Jun. 15, 2000.

(51) Int. Cl.
*A61K 31/175*    (2006.01)
(52) U.S. Cl. .................................. 514/589; 514/626
(58) Field of Classification Search ................ 514/589, 514/626
See application file for complete search history.

(56) References Cited

U.S. PATENT DOCUMENTS

| | | | | |
|---|---|---|---|---|
| 4,134,918 | A * | 1/1979 | Bey et al. | .................... 564/340 |
| 4,139,563 | A | 2/1979 | Metcalf et al. | |
| 4,267,374 | A | 5/1981 | Metcalf et al. | |
| 4,323,704 | A | 4/1982 | Metcalf et al. | |
| 5,432,202 | A * | 7/1995 | Cherksey et al. | ............ 514/626 |
| 5,633,230 | A | 5/1997 | Twist et al. | |
| 5,677,349 | A | 10/1997 | Gilad et al. | |
| 6,150,419 | A * | 11/2000 | Fairbanks et al. | ........... 514/634 |
| 6,297,281 | B1 * | 10/2001 | Chabrier de Lassauniere et al. | .......................... 514/589 |
| 6,441,156 | B1 * | 8/2002 | Lerman et al. | ............. 536/23.5 |

FOREIGN PATENT DOCUMENTS

WO    WO98/09653    *    3/1998

OTHER PUBLICATIONS

Rajasekaran et al, Effect of acute and repeated administration of nitric oxide . . . , 6th internet world congress for Biomedical science, 2000, see p. 3.*
Seeley et al, Histamine H2-receptor modulation in two mouse models of seizure . . . , Inflammation Research (1999), vol. 48(Supp.1), pp. S67-S68.*
Wada et al., Effects of the 5-HT3 receptor agonist . . . , Brain Research , 1997, vol. 759, pp. 313-316.*
Uzbay et al., Effect of agmatine on ethanol withdrawal . . . , Behavioural Brain Research, 2000, vol. 107, pp. 153-159.*
Rajasekaran et al., Effect of acute and repeated administration of NO . . . , 6th internet World congress for biomedical science(poster 129), 2000.*

The Merck Index, Merck Research Laboratories Division of Merck & Co., Inc. 1996, p. 35.
James O. McNamara, "Drugs Effective in Therapy of the Epilepsies", Goodman & Gilman's The Pharmacological Basis of Therapeutics, Ninth Edition, Chapter 20, pp. 461-486, 1996.
I. Tayfun Uzbay et al., "Effects of agmatine on ethanol withdrawal syndrome in rats", Behavioural Brain Research 107, (2000), pp. 153-159.
O. Carter Snead III, "Pharmacological models of generalized absence seizures in rodents", J. Neural Transm (1992) [Suppl], 35, pp. 1-19.
Gen Li et al., "Agmatine: An Endogenous Clonidine-Displacing Substance in the Brain", vol. 263, Feb. 18, 1994, pp. 966-969.
Mark J. Lortie et al., "Agmatine, a Bioactive Metabolite of Aginine", The American Society for Clinical Investigation, Inc., vol. 97, No. 2, Jan. 1996, pp. 413-420.
Jeremiah Morrissey et al., "Partial cloning and characterization of an arginine decarboxylase in the kidney", Kidney International, vol. 47, (1995) pp. 1458-1461.
Magdalena Sastre et al., "*Metabolism of agmatine in macrophages: modulation by lipopolysaccharide and inhibitory cytokines*", Biochem. J. (1999) 330, pp. 1405-1409.
S. Regunathan et al., "*Imidazoline Receptors and Agmatine in Blood Vessels: A Novel System Inhibiting Vascular Smooth Muscle Proliferation*", The Journal of Pharmacology and Experimental Therapeutics, vol. 276, pp. 1272-1276, 1996.
S. Regunathan et al., "*Agmatine (decarboxylated arginine) is sysnthesized and stored in astrocytes*", Rapid Science Publishers, vol. 6, No. 14, Oct. 2, 1995, pp. 1897-1900.
Nabil Anis et al., Structure-Activity Relationships of Philanthotoxin Analogs and Polyamines on N-Methyl-D-Aspartate and Nicotinic Acetylcholin Receptors, The Journal of Pharmacology and Experimental Therapeutics, vol. 254, pp. 764-771, 1990.
D.J. Reis et al., "*Agmatine: a Novel Neurotransmitter?*", Advances in Pharmacology, vol. 42, pp. 645-649, 1998.
D.J. Reis et al., "*Agmatine: and endoenous ligand at imidazoline receptors may be a novel neurotransmitter in brain*", Journal of the Autonomic Nervous System 72 (1998) pp. 80-85.
Joseph Satriano et al., "*Agmatine Suppresses Proliferation by Frameshift Induction of Antizyme and Attenuation of Cellular Polyamine Levels*", LThe Journal of Biological Chemistry, vol. 273, No. 25, 1998, pp. 15313-15316.
Elena Galea et al., "Inhibition of mammalian nitric oxide synthases by agmatine, an endogenous polyamine formed by decarboxylation of arginine", Biochem. J. (1998) 316, pp. 247-249.

(Continued)

*Primary Examiner*—Zohreh A Fay
(74) *Attorney, Agent, or Firm*—McDermott Will & Emery LLP

(57) ABSTRACT

Pharmaceutical preparations containing of agmatine, congeners, analogs or derivatives thereof for use in preventing or treating epilepsy, seizures and other electroconvulsive disorders are provided. Embodiments include administering an effective amount of agmatine, an agmatine analog or a pharmaceutically acceptable salt thereof to a human subject in need of treatment or prevention of epilepsy, seizure or other electroconvulsive disorder to treat, reduce, or prevent the disorder in the subject.

12 Claims, 1 Drawing Sheet

OTHER PUBLICATIONS

James F. Kerwin, Jr. et al., "*Nitric Oxide: A new Paradigm for Second Messengers*", Journal of Medicinal Chemistry, vol. 38, No. 22, pp. 4344-4362, 1995.

John MacMicking et al., "*Nitric Oxide and Macrophage Function*", Annual Reviews Inc. 1997, 15, pp. 323-350.

Dennis J. Stuehr, Structure-Function Aspects in the Nitric Oxide Synthases, Annual Reviews Inc., 1997, 37, pp. 339-359.

Rene H. Levy, Ph.D. et al., "*Antiepileptic Drugs*", Third Edition, Raven Press Ltd., 1989, pp. 85-102.

Rene H. Levy et al., "*Antiepileptic Drugs*", Fourth Edition, Raven Press Ltd., 1995, pp. 91-97.

H. Steve White et al., "*Experimental Selection, Quantification, and Evaluation of Antiepileptic Drugs*", Fourth Edition, Raven Press Ltd, 1995, pp. 99-110.

White H.S. et al., "*The early identification of anticonvulsant activity: role of the maximal electroshock and subcutaneous pentylenetetrazol seizure models*", The Italian Journal of Neurological Sciences, 16, 1995, pp. 73-77.

N.W. Dunham et al, "*A Note on a Simple Apparatus for Detecting Neurological Deficit in Rats and Mice*", Journal of American Pharmaceutical Association, vol. XLVI, No. 3, Mar. 1957, pp. 208-209.

\* cited by examiner

AGMATINE AND AGMATINE ANALOGS IN THE TREATMENT OF EPILEPSY, SEIZURE, AND ELECTROCONVULSIVE DISORDERS

CROSS REFERENCE TO RELATED APPLICATIONS

This application claims priority from U.S. Provisional Patent Application Ser. No. 60/211,532, filed Jun. 15, 2000 entitled "AGMATINE AND AGMATINE ANALOGS IN THE TREATMENT OF EPILEPSY, SEIZURE, AND ELECTROCONVULSIVE DISORDERS" the entire disclosure of which is incorporated herein by reference.

FIELD OF THE INVENTION

The present invention relates to the use of agmatine and analogs thereof in the prevention and treatment of epilepsies, seizures, and other electroconvulsive disorders.

BACKGROUND OF THE INVENTION

Epilepsy is a general term describing brain disorders that are characterized by the occurrence of seizures. Epilepsy affects millions of people worldwide, and over 2.5 million individuals in the United States. For the purposes of clinical assessment, it is useful to classify patients according to the type of seizure the patient experiences.

As described in *The Pharmacological Basis of Therapeutics*, seizures can occur periodically or unpredictably. (Goodman, L. S., et al., *Goodman & Gilman's The pharmacological basis of therapeutics*. 9th ed. 1996, New York: McGraw-Hill Health Professions Division. xxi, 1905, Chapter 20). Over 30 types of epileptic seizures have been described, and they can be generally classified into two groups—partial seizures (beginning focally in a cortical site) or generalized seizures (involving both brain hemispheres from the outset). Partial seizures include simple partial, complex partial and partial with secondarily generalized tonic-clonic seizures. Generalized seizures include absence, myoclonic, atonic, tonic, clonic, and tonic-clonic (grand mal) seizures.

Hundreds of epileptic syndromes have been defined as disorders characterized by specific symptoms that include epileptic seizures. These epileptic syndromes include, but are not limited to, absence epilepsy, psychomotor epilepsy, temporal lobe epilepsy, frontal lobe epilepsy, occipital lobe epilepsy, parietal lobe epilepsy, Lennox-Gastaut syndrome, Rasmussen's encephalitis, childhood absence epilepsy, Ramsay Hunt syndrome type II, benign epilepsy syndrome, benign infantile encephalopathy, benign neonatal convulsions, early myoclonic encephalopathy, progressive epilepsy, and infantile epilepsy.

A patient may suffer from any combination of different types of seizures. Partial seizures are the most common type, and account for approximately 60% of all seizure types. Regardless of the type of epilepsy, seizures significantly limit the autonomy of the patient.

It is believed that the characteristic seizures of epilepsy are caused by the disordered, synchronous and rhythmic firing of brain neurons. The neurons can fire at up to four times their normal rate. As a result, epileptic seizures are an over stimulation of the normal neuronal processes that control brain function.

Anti-epileptic drugs are available for treating epilepsies, but these agents have a number of shortcomings. For instance, the agents are often poorly soluble in aqueous and biological fluids or are extremely hygroscopic. Of even greater importance is that patients often become refractory to a drug over time. In addition, many anti-epileptic agents cause unwanted side effects, neurotoxicities, and drug interactions. Even while being treated with one or a combination of the anti-epileptic drugs currently in clinical use, 30% of epileptic patients still experience seizures. As more anti-epileptic drugs are developed, the clinician will have expanded pharmaceutical options when designing an effective treatment protocol for each patient.

U.S. Pat. No. 5,677,349 to Gilad et al. discloses methods for treating neurotrauma or neurodegenerative disease in a human by administering agmatine (4-aminobutylguanidine). Neurotrauma and neurodegeneration are terms denoting the loss of cells in the brain resulting from an external trauma or an external invasive procedure. Examples of neurodegeneration disorders include, for instance, Alzheimer's disease and Parkinson's disease, which result from the decline of neurons in the substantia nigra that produce dopamine. The neurodegenerative disorder, amyotrophic lateral sclerosis (ALS), results from the degeneration of neurons that control voluntary movement. Treatment modalities for epilepsy, however, attenuate neuronal activity, i.e., regulate the over stimulation of the neuronal processes that control brain function rather than treat cell death. Thus, it is believed that Gilad et al. have not recognized the use of agmatine in the treatment or prevention of epilepsy, seizure, and other electroconvulsive disorders.

Accordingly a continuing need exists for pharmaceutical compositions that treat or prevent epilepsy and its associated symptoms with minimal side-effects.

SUMMARY OF THE INVENTION

An advantage and object of the present invention is a pharmaceutical composition useful for the treatment, prevention and/or amelioration of disorders related to and including epilepsy, seizure and other electroconvulsive disorders.

Additional advantages and features of the invention will be set forth in part in the description which follows and in part will become apparent to those having ordinary skill in the art upon examination of the following or may be learned from the practice of the invention. The advantages of the invention may be realized and obtained as particularly pointed out in the appended claims.

According to the present invention, the foregoing objects and advantages are achieved in part by a pharmaceutical composition for the treatment or prevention of electroconvulsive disorders comprising (i) an effective amount of agmatine, an agmatine analog, or a pharmaceutically acceptable salt, complex or congener thereof and (ii) a pharmaceutically acceptable carrier. Embodiments of the present invention include a pharmaceutical composition comprising a dose of about 0.1 mg/kg to about 300 mg/kg of agmatine or its pharmaceutically acceptable salt.

Another object of the present invention is a method of treating, ameliorating, or preventing epilepsy, seizure, or electroconvulsive disorders in a subject in need thereof. Embodiments of the present invention include administering a pharmaceutical composition comprising an effective amount of agmatine, an agmatine analog, or a pharmaceutically acceptable salt thereof in a dose of about 0.1 to about 500 mg of the active agent per kilogram of a human subject's weight indefinitely or until symptoms associated with the condition or disorder cease. Additional embodiments of the present invention include identifying a human subject in need of said treatment, or prevention and preventing, or reducing epileptic activity.

Additional advantages of the present invention will become readily apparent to those skilled in this art from the following detailed description, wherein only the preferred embodiment of the present invention is shown and described, simply by way of illustration of the best mode contemplated for carrying out the present invention. As will be realized, the invention is capable of other and different embodiments, and its several details are capable of modifications in various obvious respects, all without departing from the present invention.

DESCRIPTION OF THE INVENTION

Figure 1:
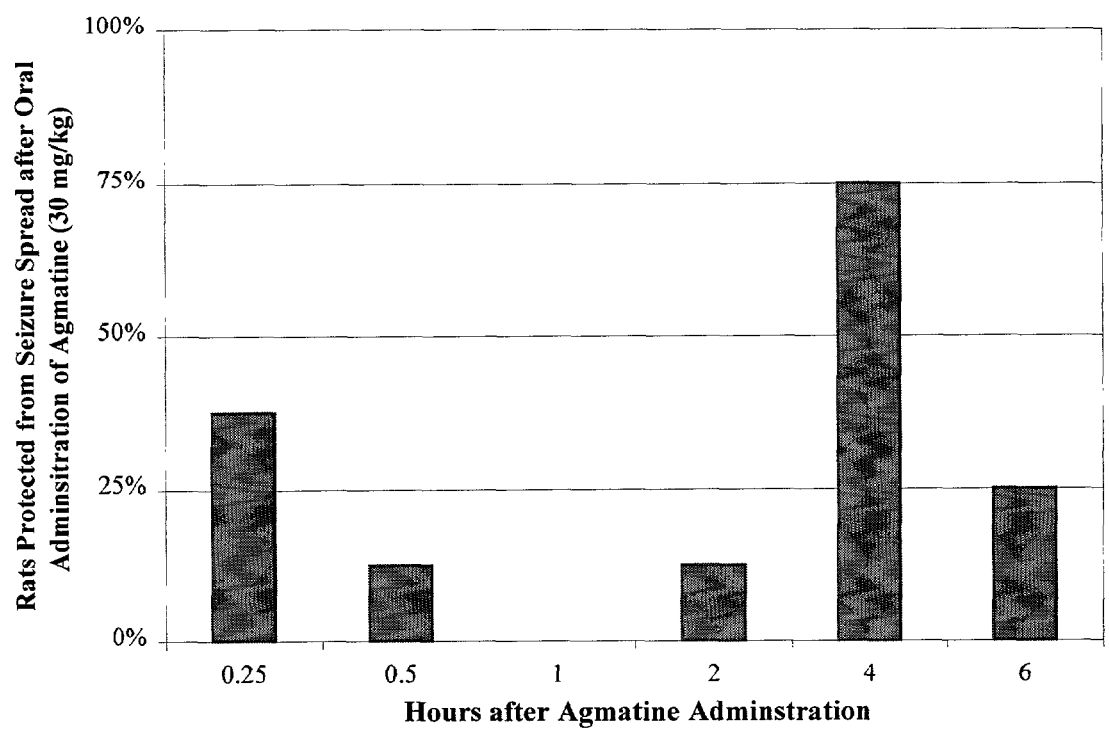
FIG. 1 graphically illustrates the effective prevention of seizure activity in accordance with an embodiment of the present invention.

The present invention relates to agmatine (Scheme 1), a naturally occurring compound, and to novel congeners, analogs, and derivatives thereof, medicating compositions containing them, and the use thereof, especially in the prevention and/or treatment of all types of seizures and other electroconvulsive disorders. Agmatine is an amine that is biosynthetically derived from the decarboxylation of L-arginine by arginine decarboxylase (ADC) (See Scheme 1).

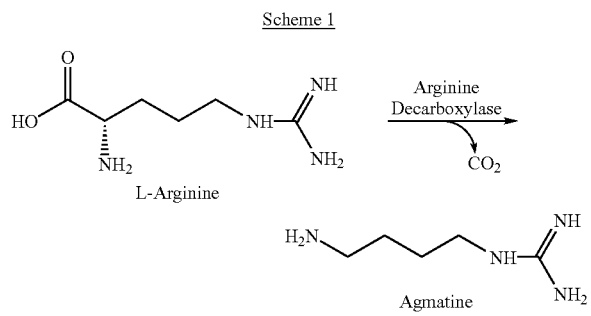

Scheme 1

The presence of agmatine in plants, bacteria, and lower life forms has been well established. Agmatine and ADC-catalyzed agmatine biosynthesis have also been detected in higher organisms, and are present in the brain, liver, kidney, adrenal gland, and small intestine of mammals. (Li, G., et al., *Agmatine: an endogenous clonidine-displacing substance in the brain*. Science (1994) 263(5149): 966-9; Lortie, M. J., et al., *Agmatine, a bioactive metabolite of arginine production, degradation, and functional effects in the kidney of the rat*, J. Clin. Invest. (1996) 97(2): 413-20; Morrissey, J., et al., *Partial cloning and characterization of an arginine decarboxylase in the kidney*, Kidney Int. (1995) 47(5): 1458-61; Sastre, M., et al., *Metabolism of agmatine in macrophages: modulation by lipopolysaccharide and inhibitory cytokines*, Biochem. J. (1998) 330(Pt 3): 1405-9). Agmatine has been detected in several types of human cells, including astrocytes, macrophages, endothelial cells and vascular smooth-muscle cells (Regunathan, S., et al., *Imidazoline receptors and agmatine in blood vessels: a novel system inhibiting vascular smooth muscle proliferation*, J. Pharmacol. Exp. Ther. (1996) 276(3): 1272-82; Regunathan, S., et al., *Agmatine (decarboxylated arginine) is synthesized and stored in astrocytes*, Neuroreport (1995) 6(14): 1897-900). These results are significant, as they indicate that mammalian agmatine is endogenously derived, and not of dietary or bacterial origin.

Although the physiological roles of agmatine are still under investigation, it is evident that agmatine exerts a wide range of biological activities, including those which may affect the function of the central nervous system (CNS). At least three possible physiological roles of agmatine have been identified. Agmatine may play a role in cell signaling, since it interacts with $\alpha_2$-adrenergic, imidazoline and N-methyl-D-aspartate (NMDA) receptors. (Li, G., et al., *Agmatine: an endogenous clonidine-displacing substance in the brain*, Science (1994) 263(5149):966-9; Anis, N., et al., *Structure-activity relationships of philanthotoxin analogs and polyamines on N-methyl-D-aspartate and nicotinic acetylcholine receptors*, J. Pharmacol. Exp. Ther. (1990) 254(3):764-73). Consequently, it has been hypothesized that agmatine may be a CNS neurotransmitter or neuromodulator in neurons involved in behavioral and visceral control. (Reis, D. J. and S. Regunathan, *Agmatine: a novel neurotransmitter?* Adv. Pharmacol. (1998) 42:645-9; Reis, D. J. and S. Regunathan, *Agmatine: an endogenous ligand at imidazoline receptors may be a novel neurotransmitter in brain*. J. Auton. Nerv. Syst. (1998) 72(2-3):80-5).

Another physiological role of agmatine is that of regulating polyamine synthesis. By inducing the synthesis of antizyme, agmatine inhibits the enzyme ornithine decarboxylase, the rate-limiting enzyme in polyamine biosynthesis. (Satriano, J., et al., *Agmatine suppresses proliferation by frameshift induction of antizyme and attenuation of cellular polyamine levels*, J. Biol. Chem. (1998) 273(25):15313-6). Polyamines exert a wide range of activities in numerous organ systems, including the central nervous system. Polyamines regulate cell proliferation, modulate postsynaptic receptors (such as NMDA, nicotinic, and benzodiazepine receptors), and have antiplatelet, anti-inflammatory, and anticoagulant activity. In addition, agmatine is a competitive inhibitor of nitric oxide synthase isoenzymes. (Galea, E., et al., *Inhibition of mammalian nitric oxide synthases by agmatine, an endogenous polyamine formed by decarboxylation of arginine*, Biochem. J. (1996) 316(Pt 1):247-9). The cell signaling and neuromodulatory properties of nitric oxide have been extensively reviewed. (Kerwin, J. F., et al., *Nitric oxide: a new paradigm for second messengers*, J. Med. Chem. (1995) 38(22):4343-62; MacMicking, J., et al., *Nitric oxide and macrophage function*, Ann. Rev. Immunol. (1997) 15:323-50; Stuehr, D. J., *Structure-function aspects in the nitric oxide synthases*, Ann. Rev. Pharmacol. Toxicol. (1997) 37:339-59).

After experimentation and investigation, it was discovered that administration of exogenous agmatine to rats resulted in profound and reproducible anticonvulsant or antiepileptic activity in animal models of seizure disorders. It was further discovered that, despite the integral role that agmatine appears to play in the function of the central nervous system and other organ systems, no toxic effects were observed in any of the animal studies as a result of the systemic administration of agmatine.

These discoveries contributed to the present invention where it is contemplated that a human subject suffering from or susceptible to epilepsy, seizure and other electroconvulsive disorders can be treated by administering a pharmaceutical composition including an effective amount of agmatine, an agmatine analog, or a pharmaceutically acceptable salt thereof to treat, reduce, or prevent the disorder in the subject. In one aspect of the present invention, a human subject is identified as having or being susceptible to the disorder prior to the administration of the active agent.

The diagnosis of a human subject that is susceptible or in need of such treatment is well known in the medical arts and includes, for example, genetic analysis, electrophysiological analysis, genealogy, etc. The diagnosis can include obtaining and analyzing a potential human subject's electroencephalogram (EEG), as is known in the art, to determine the susceptibility of seizure or the actual occurrence of a seizure. The diagnosis can also include observing the characteristic manifestations, symptoms, or features associated with the various forms of epileptic seizures. The observation can be made by the subject himself or herself, a medical practitioner or any other observer capable of making such observations and determinations. Illustrative characteristic features of various epileptic seizures are presented in Table 1 below.

TABLE 1

| SEIZURE TYPE | FEATURES |
|---|---|
| Simple partial | Diverse manifestations determined by the region of cortex activated by seizure (e.g., if motor cortex representing left thumb, clonic jerking of left thumb results; if somatosensory cortex representing left thumb, paresthesias of left thumb results), lasting approximating 20 to 60 seconds. A key feature is preservation of consciousness. |
| Complex partial | Impaired consciousness lasting about 30 seconds to about one to about two minutes, often associated with purposeless movements such as lip smacking or hand wringing. |
| Partial with secondarily generalized tonic-clonic seizure | Simple or complex partial seizure evolves into a tonic-clonic seizure with loss of consciousness and sustained contractions (tonic) of muscles throughout the body followed by periods of muscle contraction alternating with periods of relaxation (clonic), typically lasting about 1 to 2 minutes. |
| Absence seizure | Abrupt onset of impaired consciousness associated with starting and cessation of ongoing activities typically lasting less than 30 seconds. |
| Myoclonic seizure | A brief (perhaps a second), shock-like contraction of muscles which may be restricted to part of one extremity or may be generalized. |
| Tonic-clonic seizure | As described above for partial with secondarily generalized tonic-clonic seizures except that it is not preceded by a partial seizure. |

In practicing the present invention, agmatine, an agmatine analog, or a pharmaceutically acceptable salt, complex or cogener thereof is formulated into a pharmaceutical preparation comprising the active agent and a pharmaceutically acceptable carrier. It has been discovered that the inventive compositions are useful in the prevention, palliation and/or treatment of seizures, conduction disturbances, and electroconvulsive disorders of all types, and their manifestations irrespective of the origin of the aliment in a subject in need thereof including humans and other mammals. It is contemplated that the inventive compositions can be employed for preventing and/or treating other conduction disturbances of the CNS, and the emotional, cognitive, and motor symptoms resulting therefrom.

In an embodiment of the present invention, the inventive compositions are administered to a subject, e.g. a human subject, in need thereof to prevent or treat disturbances of the CNS, such as seizure and electroconvulsive disorders, of either or both an acute or chronic nature, of unknown origin or secondary to conditions such as, but not limited to: surgery, irradiation or other manipulation of the brain and/or CNS; alcohol, benzodiazepine, barbiturate or other drug or chemical withdrawal; exposure to epileptogenic drugs and/or chemicals; acute or chronic injury or trauma; stroke or cerebrovascular accident; fever; meningitis or other CNS inflammation or infection; or electroconvulsive therapy.

In practicing the present invention, agmatine, an agmatine analog, or a pharamceutically acceptable salt thereof is formulated into a pharmaceutical composition. In an embodiment of the present invention, agmatine and agmatine analogs are provided by Formula I below:

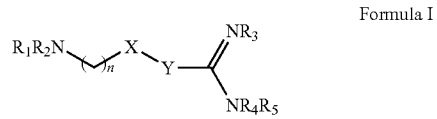

Formula I wherein n is 0 to about 10; $R_1$, $R_2$, $R_3$, $R_4$, and $R_5$, are each independently, or any combination thereof: hydrogen, hydroxy, substituted or unsubstituted $C_{1-10}$ alkyl, substituted or unsubstituted $C_{3-8}$ cycloalkyl, substituted or unsubstituted arylalkyl (comprising Ar—$(CH_2)_m$; where Ar is aromatic and m is 0 to about 10) substituted or unsubstituted $C_{1-10}$ alkoxyl, substituted or unsubstituted $C_{1-10}$ acyl, halogeno, amido, phenyl, thio, amino, or nitro including racemic, diastereomeric, and all enantiomeric forms. In a preferred embodiment, $R_1$ and $R_2$ represent $R_1$—$(CH_2)_n$—$R_2$ where n is 3-8 and $R_3$ and $R_5$ represent $R_3$—$(CH_2)_n$—$R_5$ where n is 3-8. X and Y are each independently: O, NH, $CH_2$, $CF_2$, Se, C=O, C=N, C=S, or S; or X—Y together is HC=CH, C≡C, N=N, N=CH, CH=N, or a saturated or unsaturated ring including all geometric and stereoisomers thereof.

In an embodiment of the present invention, X—Y is a saturated ring including, but not limited to: cyclobutane, cyclopentane, cyclohexane, cycloheptane, cyclooctane, azetine, piperdine, pyrazolidine, imidazoline, piperazine, piprazine, hexa-hydropyrimidine, thietane, thiophane, 1,3-dithiolane, 1,2-dithiolane, thiane, 1,2-dithiane, 1,3-dithane, 1,4-dithiane, tetrahydrofuran, tetrahydropyran, 1,4-dioxane, 1,3-dioxane and 1,4-oxathinin, oxetane, morpholine, imidazoline, oxazoline, and thiazolidine, including all possible substitution patterns, geometric and stereoisomers, racemic, diastereomeric and enantiomeric forms thereof.

In an embodiment of the present invention, X—Y is an unsaturated hydrocarbon ring including, but not limited to benzene, cyclopentene, cyclohexene, cycloheptene, cyclooctene, cyclopentadiene, including all possible substitution patterns, geometric and stereoisomers, racemic, diastereomeric, and enantiomeric forms thereof.

In an embodiment of the present invention, X—Y is an unsaturated nitrogen heterocycle, including but not limited to, pyrrole, pyrrolidine, pyrazole, imidazole, 1,2,3-triazole, 1,2,4-triazole, pyridine, pyridazine, pyrimidine, pyrazine, triazine, indole, indazole, pteridine, quinoline, quinazoline, benzodiazepine, acridine, benzimidazole, purine, isoquinazoline, and isoquinoline, including all possible substitution patterns, geometric and stereoisomers, racemic, diastereomeric and enantiomeric forms thereof.

In an embodiment of the present invention, X—Y is an unsaturated oxygen heterocycle, including but not limited to furan, 2,5-dihydrofuran, or pyran including all possible substitution patterns, geometric and stereoisomers, racemic, diastereomeric, and enantiomeric forms thereof.

In an embodiment of the present invention, X—Y is an unsaturated sulfur containing heterocycle, including but not limited to, thiophene, 2,5-dihydrothiophene, 1,2-dithiolylium, 1,3-dithiolylium, thiopyranylium, including all possible substitution patterns, geometric and stereoisomers, racemic, diastereomeric, and enantiomeric forms thereof.

In an embodiment of the present invention, X—Y is an unsaturated selenium containing heterocycle, including but not limited to selenophene including all possible substitution patterns, geometric and stereoisomers, racemic, diastereomeric, and enantiomeric forms thereof.

In an embodiment of the present invention, X—Y is an unsaturated mixed heterocycle, including but not limited to thiazole, benzothiazole, benzoxazole, thiadiazole, phenothiazine, isoxazole, 2-oxazoline, oxazole and oxazin including all possible substitution patterns, geometrical, and stereoisomers, racemic, diastereomeric and enantiomeric forms thereof.

Agmatine can be isolated from naturally occurring sources or synthetically prepared by conventional techniques. Agmatine analogs can be synthetically prepared by conventional synthesis as disclosed by U.S. Pat. No. 5,677,349 the entire disclose of which is hereby incorporated by reference.

Salt forms of agmatine and its analogs include, but are not limited to, the following: inorganic acid addition salts such as hydrochloride, hydrobromide, sulfate, phosphate, and nitrate; organic acid addition salts such as acetate, galactarate, propionate, succinate, lactate, glycolate, malate, tartrate, citrate, maleate, fumarate, methanesulfonate, salicylate, p-toluenesulfonate, benzenesulfonate, and ascorbate; salts with acidic amino acids such as aspartate and glutamate; the salts may be in some cases hydrates or solvates with alcohols and other solvents. Salt forms of agmatine for an agmatine analog can be prepared by admixing the acid with agmatine for its analog in a conventional solvent or equivalent thereof, with or without alcohols or water.

The compounds of the present invention are useful in pharmaceutical compositions for systemic administration to mammals including humans as a single agent, or as a primary or adjunct agent with any other medication, chemical, drug or non-drug therapy, or combination thereof.

The aforementioned administration of agmatine, agmatine analogs or pharmaceutically acceptable salt thereof is to be employed acutely, or as a single dose, or administered intermittently, or on a regular schedule of unspecified duration, or by continuous infusion of unspecified duration, by any acceptable route of administration including, but not limited to, parenteral, oral, buccal, intranasal, pulmonary, transdermal, rectal, vaginal, intradermal, intrathecal, intravenous, intramuscular and/or subcutaneous routes.

The pharmaceutical preparations can be employed in unit dosage forms, such as tablets, capsules, pills, powders, granules, suppositories, sterile parenteral solutions or suspensions, sterile non-parenteral solutions or suspensions oral solutions or suspensions, oil in water or water in oil emulsions and the like, containing suitable quantities of an active ingredient. Topical application can be in the form of ointments, creams, lotions, jellies, sprays, douches, and the like. For oral administration either solid or fluid unit dosage forms can be prepared with the compounds of Formula I.

Either fluid or solid unit dosage forms can be readily prepared for oral administration. For example, the compounds can be mixed with conventional ingredients such as dicalciumphosphate, magnesium aluminum silicate, magnesium stearate, calcium sulfate, starch, talc, lactose, acacia, methyl cellulose and functionally similar materials as pharmaceutical excipients or carriers. A sustained release formulation may optionally be used. Capsules may be formulated by mixing the compound with a pharmaceutical diluent, which is inert and inserting this mixture into a hard gelatin capsule having the appropriate size. If soft capsules are desired, a slurry or other dispersion of the compound with an acceptable vegetable, light petroleum, or other inert oil can be encapsulated by machine into a gelatin capsule.

Suspensions, syrups, and elixirs may be used for oral administration of fluid unit dosage forms. A fluid preparation including oil may be used for oil soluble forms. A vegetable oil such as corn oil, peanut oil, or safflower oil, for example, together with flavoring agents, sweeteners and any preservatives produces an acceptable fluid preparation. A surfactant may be added to water to form a syrup for fluid unit dosages. Hydro-alcoholic pharmaceutical preparations may be used having an acceptable sweetener such as sugar, saccharine, or a biological sweetener and a flavoring agent in the form of an elixir.

Pharmaceutical compositions for parenteral and suppository administration can also be obtained using techniques standard in the art. Another preferred use of the compounds is in a transdermal parenteral pharmaceutical preparation in a mammal such as a human.

The above and other drugs can be present in the reservoir alone or in combination form with pharmaceutical carriers. The pharmaceutical carriers acceptable for the purpose of this invention are the art known carriers that do not adversely affect the drug, the host, or the material comprising the drug delivery device. Suitable pharmaceutical carriers include sterile water; saline, dextrose; dextrose in water or saline; condensation products of castor oil and ethylene oxide combining about 30 to about 35 moles of ethylene oxide per mole of castor oil; liquid acid; lower alkanols; oils such as corn oil; peanut oil, sesame oil and the like, with emulsifiers such as mono- or di-glyceride of a fatty acid, or a phosphatide, e.g., lecithin, and the like; glycols; polyalkylene glycols; aqueous media in the presence of a suspending agent, for example, sodium carboxymethylcellulose; sodium alginate; poly(vinylpyrolidone); and the like, alone, or with suitable dispensing agents such as lecithin; polyoxyethylene stearate; and the like. The carrier may also contain adjuvants such as preserving stabilizing, wetting, emulsifying agents and the like together with the penetration enhancer of this invention.

By "effective amount", "therapeutic amount" or "effective dose" is meant that amount sufficient to elicit the desired pharmacological or therapeutic effects, thus resulting in effective prevention or treatment of the condition or disorder. Thus, when treating a CNS disorder, an effective amount of a compound is that amount sufficient to pass across the blood-brain barrier of the subject to bind to relevant receptor sites in the brain of the subject or otherwise affect the brain. Prevention of the condition or disorder is manifested by delaying the onset of the symptoms of the conditions or disorder. Treatment of the condition or disorder is manifested by a decrease in the symptoms associated with the condition or disorder, or an amelioration of the recurrence of the symptoms of the condition or disorder.

The effective dose can vary, depending upon factors such as the condition of the patient, the severity of the symptoms of the disorder, age, weight, and the manner in which the pharmaceutical composition is administered. Typically, the effective dose of compounds generally requires administering the compound in an amount of about 0.1 to about 500 mg per kilogram of the subject's weight. In an embodiment of the present invention, the a dose of about 0.1 to about 300 mg/kg is administered per day indefinitely or until symptoms associate with the condition or disorder cease. Preferably about 1.0 to about 50 mg per kilogram body weight is administered per day. The required dose is less when administered parenterally.

EXAMPLES

Example 1

The Maximal Electroshock Seizure (MES) or Maximal Seizure Pattern Test

The MES is an experimental model for generalized tonic-clonic seizures that identifies compounds which prevent seizure spread. The MES model is highly reproducible and has a consistent endpoint. An advantage of this model is that the behavioral and electrographic seizures are consistent with those observed in humans (Levy, R. H., *Antiepileptic drugs*. 3rd Ed. 1989, New York: Raven Press. xxvii, 1025. p. 85-102).

In the MES test, the animal receives an electrical stimulus, 0.2 seconds in duration, via corneal electrodes primed with an electrolyte solution containing an anesthetic agent. The 0.2 second stimulation is generated with 150 mA in rats at 60 Hz. Twenty rats, weighing between 105 g and 130 g receive an electrical stimulus 15 minutes, 30 minutes, 1 hour, 2 hours, 4 hours, 8 hours and 12 hours after oral administration of a dose of about 30 mg/kg of agmatine in phosphate buffered in saline per kg of the animal. The test endpoint, electrogenic seizure, is manifested as hindlimb tonic extension. Inhibition of hindlimb tonic extension indicates that the test compound is able to inhibit MES-induced seizure spread which in turn is indicative of antiseizure activity (Levy, R. H., *Antiepileptic drugs*. 3rd Ed. 1989, New York: Raven Press. xxvii, 1025. p. 85-102; Levy, R. H., et al., *Antiepileptic drugs*. 4th Ed. 1995, New York: Raven Press. xxv, 1120. p. 99-110; White, H. S., et al., *The early identification of anticonvulsant activity: role of the maximal electroshock and subcutaneous pentylenetetrazol seizure models*. Ital. J. Neurol. Sci. (1995) 16(1-2):73-7).

The results of the MES test demonstrate that agmatine is effective in preventing seizure spread in the rat. As shown in FIG. 1, an oral agmatine dose of 30 mg/kg prevented seizure spread in 37.5% of the rats which received a shock 0.25 hours after agmatine administration. At 0.5 hours after agmatine administration, 12.5% of the rats were protected, while at 1 hour after oral agmatine administration, none of the rats were protected from seizure spread after receiving the electrical stimulus. Notably, at 2, 4, and 6 hours after agmatine administration, protection from MES-induced seizure spread was again observed as 12.5%, 75% and 25%, respectively, of the animals in each group. These data indicate that the oral administration of agmatine (30 mg/kg) may have both acute (0-1 hours) and delayed (2-6 hours) inhibitory effects on MES-induced seizure spread. Additionally, the administration of intraperitoneal agmatine 4 hours before receiving an electrical shock prevented seizure spread in 50% of rats so treated, indicating that the protection from MES-induced seizures by agmatine can be observed when the compound is give via a route other than the oral route.

Example 2

Minimal Neurotoxicity

Toxicity in mice and rats is assessed using three screens: the rotorod in mice, positional sense, and gait in rats. In mice, the test compound is administered at doses of 30, 100, and 300 mg/kg prior to evaluation in the toxicity screens. The mice are tested 0.5 hours and 4 hours after administration of the test compound. In rats, the test compound is administered at 30 mg/kg prior to the toxicity assessment. The rats are tested at 0.25, 0.5, 1, 2, and 4 hours after administration of the test compound.

Rotorod Test

Toxicity in mice weighing between 20.5 and 25.5 g is assessed using the standardized rotorod test (Dunham, M. S. and T. A. Miya, *A note on a simple apparatus for detecting neurological deficit in rats and mice*, J. Am. Pharm. Assoc. Sci. Edit (1957) 46:208-209). Control mice can maintain their equilibrium for an extended period of time when they are placed on a 6 rpm rotation rod. Neurologically impaired animals cannot maintain equilibrium for one minute in each of three successive trials.

Positional Sense Test

Behavioral toxicity in rats weighing between 105 and 130 g is assessed by the positional sense test. In this test, one hind leg is gently lowered over the edge of a table. If the rat experiences neurological toxicity, it will not be able to quickly lift its leg back to a normal position.

Gait and Stance Test

In the gait and stance test, neurotoxicity is indicated by a circular or zigzag gait after administration of the test compound. In addition, ataxia, abnormal spread of the legs, abnormal posture, tremor hyperactivity, lack of exploratory behavior, somnolence, stupor, or catalepsy can indicate neurotoxicity. This toxicity test was conducted on 20 rats, weighing between 105 and 130 g.

In rats and mice, agmatine was demonstrated to be devoid of any neurological toxicity related to the assays described above. Twenty-four mice, received agmatine doses as high as 300 mg/kg. As quantified by the rotorod neurotoxicity test, none of these animals showed any evidence of behavioral or neurotoxicity. Similarly, agmatine showed no neurotoxicity in rats. Forty rats received either oral or intraperitoneal agmatine at a dose of 30 mg/kg. As assessed by the positional sense and the gait and stance tests, these data suggest that agmatine is not neurotoxic.

While the present invention has been described in connection with what is presently considered to be the most practical and preferred embodiments, it is to be understood that the invention is not limited to the disclosed embodiments and examples. It should be apparent to those of skill in the art that various modifications and variations may be made to the composition and method of the present invention without departing from the spirit or scope of the invention. All relevant portions of patents and publications cited herein are incorporated by reference in their entireties.

What is claimed is:

1. A method of treating, ameliorating, or preventing seizures associated with epilepsy in a subject in need thereof, the method comprising:

administering a pharmaceutical composition comprising about 0.1 to about 500 mg of agmatine or an agmatine analog, or a pharmaceutically acceptable salt thereof per kilogram of the subject's weight to treat, reduce, or prevent seizures associated with epilepsy in the subject, wherein the agmatine analog has the following formula

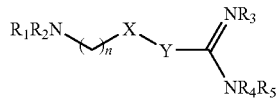

wherein n is 0 to about 10;

$R_1$, $R_2$, $R_3$, $R_4$, and $R_5$, are each independently, or any combination thereof: hydrogen, hydroxy, substituted or unsubstituted $C_{1-10}$ alkyl, substituted or unsubstituted $C_{3-8}$ cycloalkyl, substituted or unsubstituted arylalkyl (comprising Ar—$(CH_2)_m$; where Ar is aromatic and m is 0 to about 10) substituted or unsubstituted $C_{1-10}$ alkoxyl, substituted or unsubstituted $C_{1-10}$ acyl, halogeno, amido, phenyl, thio, or amino; and X and Y are each independently: O, NH, $CH_2$, $CF_2$, Se, C=O, C=N, or C=S, or X—Y together is HC=CH, C=C, N=N, N=CH, CH=N, or a saturated or unsaturated ring.

2. A method according to claim 1, wherein the pharmaceutical composition comprises agmatine or its pharmaceutically acceptable salt and a pharmaceutically acceptable carrier.

3. A method according to claim 2, wherein the composition is administered in a dose of about 0.1 to about 50 mg/kg per day indefinitely or until seizures associated with the epilepsy.

4. A method according to claim 1, comprising preventing or reducing seizure activity.

5. A method of treating or preventing seizures associated with epilepsy in a human comprising:
   identifying a human subject in need of said treatment or prevention; and
   administering about 0.1 to about 500 mg of agmatine or an agmatine analog, or a pharmaceutically acceptable salt thereof per kilogram of the subject's weight to the human subject, wherein the agmatine analog has the following formula

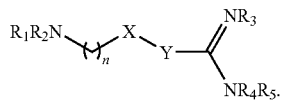

wherein n is 0 to about 10;

$R_1$, $R_2$, $R_3$, $R_4$, and $R_5$, are each independently, or any combination thereof: hydrogen, hydroxy, substituted or unsubstituted $C_{1-10}$ alkyl, substituted or unsubstituted $C_{3-8}$ cycloalkyl, substituted or unsubstituted arylalkyl (comprising Ar—$(CH_2)_m$; where Ar is aromatic and m is 0 to about 10) substituted or unsubstituted $C_{1-10}$ alkoxyl, substituted or unsubstituted $C_{1-10}$ acyl, halogeno, amido, phenyl, thio, or amino; and X and Y are each independently: O, NH, $CH_2$, $CF_2$, Se, C=O, C=N, or C=S, or X—Y together is HC=CH, C=C, N=N, N=CH, CH=N, or a saturated or unsaturated ring.

6. A method according to claim 5, comprising identifying a human subject in need of said treatment by analyzing an electroencephalogram taken of the human subject.

7. A method according to claim 5, comprising identifying a human subject in need of said treatment by observing the occurrence of a seizure in said subject.

8. A method according to claim 5, comprising administering the effective amount of agmatine, an agmatine analog or a pharmaceutically acceptable salt thereof to the human subject indefinitely or until the seizures associated with epilepsy cease.

9. A method according to claim 5, comprising preventing or reducing seizures associated with epileptic activity.

10. A method according to claim 5, comprising administering the effective amount of agmatine, an agmatine analog or a pharmaceutically acceptable salt thereof as a pharmaceutical composition.

11. A method according to claim 5, comprising administering the effective amount of agmatine, an agmatine analog or a pharmaceutically acceptable salt thereof parenterally.

12. A method according to claim 5, comprising administering the effective amount of agmatine, an agmatine analog or a pharmaceutically acceptable salt thereof orally.

* * * * *